(12) United States Patent
Bass

(10) Patent No.: US 8,236,334 B2
(45) Date of Patent: Aug. 7, 2012

(54) COMPOSITION AND METHOD FOR KILLING INSECTS

(76) Inventor: James S. Bass, Fort Myers, FL (US)

( * ) Notice: Subject to any disclaimer, the term of this patent is extended or adjusted under 35 U.S.C. 154(b) by 50 days.

(21) Appl. No.: 11/218,739

(22) Filed: Sep. 6, 2005

(65) Prior Publication Data

US 2007/0053945 A1    Mar. 8, 2007

(51) Int. Cl.
*A01N 25/02* (2006.01)
(52) U.S. Cl. ......... 424/405; 47/57.5; 424/408; 424/409; 424/417; 514/87; 514/89; 514/122; 514/195.18; 514/199; 514/210.05; 514/380; 514/619; 514/645; 514/747
(58) Field of Classification Search .................. None
See application file for complete search history.

(56) References Cited

U.S. PATENT DOCUMENTS

| | | | | |
|---|---|---|---|---|
| 1,999,458 | A * | 4/1935 | Hollister | 47/57.5 |
| 2,083,984 | A * | 6/1937 | Buchanan | 424/416 |
| 3,254,449 | A * | 6/1966 | Mauget | 47/57.5 |
| 6,296,880 | B1 * | 10/2001 | Murad | 424/616 |
| 6,335,325 | B1 * | 1/2002 | Bretschneider et al. | 514/211.15 |
| 6,911,211 | B2 * | 6/2005 | Eini et al. | 424/401 |
| 7,070,806 | B2 * | 7/2006 | Oshlack et al. | 424/468 |
| 7,232,844 | B2 * | 6/2007 | Hallahan | 514/456 |
| 2001/0051174 | A1 * | 12/2001 | Staats | 424/405 |
| 2004/0170660 | A1 * | 9/2004 | Wendel et al. | 424/405 |
| 2005/0118280 | A1 | 6/2005 | Leach et al. | |
| 2005/0153841 | A1 * | 7/2005 | Bunt et al. | 504/366 |
| 2006/0264328 | A1 * | 11/2006 | Modaressi et al. | 504/165 |
| 2007/0166340 | A1 * | 7/2007 | Stringfellow | 424/405 |

FOREIGN PATENT DOCUMENTS

| | | | |
|---|---|---|---|
| WO | WO 95/20877 | * | 12/1995 |
| WO | WO 98/18610 A1 | | 5/1998 |

OTHER PUBLICATIONS

PENA—Abstract of proc. Fla. state HORTIC. Soc. (105. 286-287, 1992) Chemical Control of Avocado & Lime Pests.*
International Search Report mailed Sep. 27, 2007 issued in International Application No. PCT/US06/38993.
Translation of the International Preliminary Report on Patentability of International Application No. PCT/US2006/038993, dated Apr. 16, 2009 with Form PCT/IB/373 and Form PCT/ISA/237.

* cited by examiner

*Primary Examiner* — Neil Levy
(74) *Attorney, Agent, or Firm* — Westerman, Hattori, Daniels & Adrian, LLP

(57) ABSTRACT

Disclosed is a method for protecting a tree from insects by injecting the tree with a fungicide and/or an antibiotic, and applying a composition to the surface of the tree, said composition comprising water, an insect repellent, an antihistamine, and an insect poison.

16 Claims, No Drawings

COMPOSITION AND METHOD FOR KILLING INSECTS

BACKGROUND OF INVENTION

The control of insects, particularly boring insects is one of man's oldest problems. During modern times, the most effective controls of insects has been through the use of large amounts of toxic chemicals or insecticides. However, such insecticides, used in high volumes, have had serious side effects, such as the simultaneous killing of beneficial insects, such as bees and other insects which are predators of less beneficial pests. The widespread use of insecticides has further resulted in the killing of other wildlife, such as birds and small rodents as well as detrimental effects to human kind (i.e., human exposure to DDT).

More modern efforts have tried to utilize biological means which control insects but do not harm other wildlife or beneficial insects. Such controls include the use of bacteria which infects only a specific insect being controlled. However, these biological controls do not appear to be the complete answer either. Although they are more friendly to the environment, not all insects are susceptible to biological controls and in many cases, the control is not completely effective.

Other species of insects have resisted all attempts to control them. Particularly resistant are those insects found to bore tunnels within, and sometimes through the internal portion of trees. Application of insecticide to these areas has proven to be most difficult and sometimes affects the life cycle and health of the tree and other life forms in close proximity.

Other attempts to control insects by providing some degree of efficiency prove ineffective to control crawling insects. An example of such alternative ineffectual insect controls is the electrical exterminator which is a trap having an electrode grid surrounding an insect attracting element, such as a light. As the insects attempt to reach the light, they encounter electrodes which shorts out the insect's body thereby electrocuting the insect. Consequently, electrical insect exterminators are limited to flying insects which would include moths, not necessarily caterpillars or larvae insects which bore through into trees prior to metamorphose into flying insects.

Still other attempts at controlling insect infestation have been tried, in which an insecticidal coating having an extended residual period of a few months to a year is applied to a surface. A removable cover may be positioned near the surface to create a substantially darkened region to exploit some insects' natural tendencies to hide in dark places during daylight hours. Alternatively, the insecticide may be applied prior to the hatching of the insect eggs to control the population upon hatching. The method is said to be especially effective for controlling the presence of gypsy moth caterpillars on trees, but suffers from the cost and time required by the covers.

These and other difficulties experienced with prior art devices have been obviated in a novel manner by the present invention. It is therefore one object of the instant invention to provide an environmentally sound and friendly method to eradicate or remove insects restively accommodated within a bored tunnel structure located in the internal portion of a tree or other similarly composed structures, including other plants and shrubs and even lumber. Certain embodiments of the instant invention may be used to attack specific plant predators and/or their hiding places. Other embodiments are particularly suited for controlling or even eradicating fungal and/or bacterial infections.

SUMMARY OF THE INVENTION

The present inventor has discovered a method for killing insects, as well as fungal and/or bacterial infections, which overcomes the difficulties described above. The method includes the steps of (1) injecting or spraying a tree or shrub with a fungicide and/or an antibiotic to kill the fungus and/or bacteria which larva or mature insects use for nutrition, and (2) applying to the surface of the tree, including its branches and foliage, a composition comprising water, poison, an insect repellent, and an antihistamine.

Although the inventor is not committed to a particular theory of operation, he believes that that the fungicide and/or antibiotic kill(s) the fungus and/or bacteria which the larva or mature insects use for nutrition. Again, the inventor is not committed to a theory of operation, but he believes that the antihistamine carries the composition, including the repellent and the poison past the immune systems of the tree or other plants such as shrubs into the interior to the insects, and that the repellent forces the insects to try to escape from the interior of the tree by eating their way toward the outer edges of the tree, thereby ingesting the poison that kills the insects. The inventor believes that mode of administering poison targets the harmful insects, as opposed to other insects and is therefore effective at lower poison strengths than was previously possible.

DETAILED DESCRIPTION OF THE INVENTION

The composition for use in this invention preferably comprises water which permits spraying onto trees. In addition to the water, the composition comprises a base composition which is to be applied (for instance by spraying) to the outside surface of the tree or shrub, and which comprises an insect repellent, an insect poison and an antihistamine. Some embodiments of the instant invention may be formed by combining the fungicide and/or anti-bacterial mixture with an antihistamine. Preferably, the base composition is formed first and then added to the water to form the composition of the invention, although the order in which the base composition components are added to the water is not limited. More preferably, the antihistamine may be added after all the other base composition components have been completely mixed with the carrier.

The base composition may also include a fungicide, an antibiotic or both. Preferably, the base composition is added to the water at the point of use, for instance at the moment just prior to its injection into a tree.

In the case of trees which have already been infested with the target insects, special measures should be adopted. The tree must be injected as soon as possible after detection of infestation. The holes created by the injections should then be plugged with a wooden dowel or other suitable plug, and the plug and the area surrounding the plug should be sprayed with a plant sealant. The number of injections needed can be readily determined according to the size of the tree, by one skilled in the art. To avoid creating a structural weakness within the tree from the injections, the points of injection should start near the base of the tree and swirl upward in a pattern rotating the trunk of the tree. The injections are preferably made at an angle downward from horizontal and preferably reach the heart-wood. Only in unusual cases, would it be desirable to locate all the injections on one side of the tree.

The water wetting agent may be soap or a spreader sticker. The water wetting agent and soap (preferably from an environmental point of view, lye soap) and spreader sticker are mixed with pesticide and water. The mixture is odorless and promotes the passage of the composition of the pesticide, i.e., to penetrate and stick better onto targeted areas. This is critical when treating for thrips or other woodworms because they hide deep within the tree or lumber and are therefore hard to reach.

As disclosed in U.S. Pat. No. 6,749,861, which is incorporated in its entirety herein by reference, certain fragrances repel insects and other pests. These fragrances can be impregnated on paper to form insect repellants.

The insect repellents suitable for the present invention include the following: Bay Laurel, Cedarwood, Clover flowers, Feverfew, Mesquite, Mountain Mahogany, Oil of Mint, Oil of Pennyroyal, Oil of Sassafras, Pyrethrum, Southernwood, Squaw Bush, Tonka, Vetiver, White alder, Wormwood, Rue, Sweet Birch Bark (Wintergreen, i.e., methyl salicylate), benzoic acid, Citronella, Camomile, Savory, Eucalyptus, Mugwort, Tansy, Thyme, Rose Geranium, Clove, Santolina, Sage, Camphor and Larkspur. Among these repellents, Wintergreen and Oil of Mint are believed to be preferred and Wintergreen is believed to be particularly preferred.

The selection of a particular insect repellent and the amount of the amount repellent to be used are not particularly limit, so long as it repels the insects to the extent that the insects attempt to leave the tree or lumber.

The antihistamine of the present invention includes the following: azatadine, antazoline, astemizole, brompheniramine, cetirizine, chlorpheniramine, clemastine, cyproheptadine, descarboethoxyloratadine, dexchlorpheniramine, diphenhydramine hydrochloride, diphenylpyraline, famotidine, fexofenadine, hydroxyzine, loratidine, meclizine, methdilazine, nizatidine, pheniramine pyrilamine, promethazine, and ranitidine, terfenadine, trimeprazine, tripelennamine, triprolidine. Among these antihistamines, the antihistamine in Benadril® (i.e., diphenhydramine hydrochloride) is preferred.

Malathion is an organophosphate and a preferred insect poison in the present invention. It also known as carbophos, maldison and mercaptothion. Trade names for products containing malathion include Celthion, Cythion, Dielathion, El 4049, Emmaton, Exathios, Fyfanon and Hilthion, Karbofos and Maltox. It is available in emulsifiable concentrate, wettable powder, dustable powder, and ultra low volume liquid formulations. It must also be emphasized, however, that malathion must be handled with great care. Other suitable poisons include diazinon, dursban, and sevin.

The insect poison of the present invention may also be a composition comprising at least one protease enzyme capable of exterminating insects, which enzymes are disclosed in U.S. Pat. No. 6,663,860 which is incorporated herein in its entirety by reference. The enzyme component may comprise a single protease or a protease-containing mixture of enzymes, whether natural, preformed, or synthetic.

The proteases used in the composition of a preferred embodiment of the present invention may be any of the peptidases, serine proteases, zinc proteases, thiol proteases, and/or acid proteases. The proteases may be digestive proteases from an animal, plant, bacterium, or fungus. Additional enzymes may be any of hydrolases, oxidoreductases, transferases, lyases, ligases, and/or isomerases. Additional enzymes may comprise digestive enzymes from an animal, plant, bacterium, or fungus. Preferably, the enzyme component comprises at least one protease and at least one other hydrolase, more preferably a mixture of at least one protease and at least one cellulase, lipase, glycosidase, amylase, chitinase, other protease, or mixture thereof.

The selection of a particular insect poison and the amount of the amount of the poison to be used are not particularly limit. Any poison, natural or synthetic, that will kill the target insect may be used. However, it is preferable from an efficacy point of view that the poison not break down too rapidly from sunlight or exposure to the elements. On the other hand, since the object is to target particular insects, rather than the general insect population, extremely long-lasting poisons are not preferred.

The antibiotic is not particularly limited and includes Keflex. Keflex is an antibiotic in a class of drugs called cephalosporins. Keflex is known to fight bacteria in the human body. Other suitable antibiotics include any of the penicillin group, tetracycline and any of the sulfa drugs.

The fungicides of the present invention are not particularly limited and includes benomyl, cyproconazole, imazalil and other similarly effective compounds. They may be regular fungicides or have systemic qualities. They may be in liquid, powder or granular form.

The device for injecting the composition of the present invention is not particularly limited. One preferred device is disclosed in U.S. Pat. No. 6,484,440 which is incorporated herein in its entirety by reference. Specifically, a spike, drivable into the trunk of a tree, is used. The spike includes a hollow body which provides a storage chamber for a water soluble compound such as a pesticide or fertilizer. The spike has a generally pointed first end which facilitates driving the spike into a tree trunk. The hollow body is equipped with bleed apertures near the pointed end, so that when the spike is driven into the trunk of a tree, the storage chamber is coupled to the vascular system thereof. The spike is supplied with a resilient sheath that seals the bleed apertures during shipping and handling. As the spike is driven into a tree trunk, the sheath is peeled off the body, thereby exposing the bleed apertures to the tree's vascular tissue and forming a gasket between the spike body and the aperture created by driving the spike into the trunk. It is preferred that the spike reach the heart-wood.

The insect repellent and insect poison are present in a relative proportion by volume of 20:80 to 80:20, preferably 30:70 to 70:30, most preferably 40:60 to 60:40. The antihistamine is present in an amount by volume of 0.1-20% based on the total base composition before the addition of water, preferably 2-10%, most preferably 4-6%.

Steroids may also be added to injection composition or the spray composition to promote healing of the tree. Rodent repellents, such as Hound's Tongue, may be included in the spray composition.

The following examples are intended to be illustrative, and not limiting, of the present invention.

EXAMPLES

A preferred base composition for use in the present invention may be prepared by mixing the following ingredients:

| (1) | soap | 150 ml |
| (2) | diphenhydramine hydrochloride | 4 teaspoons |
| (3) | Wintergreen | ¼ cup |
| (4) | insect poison | ¼ cup |
| (5) | liquid copper | 2 tablespoons |
| (6) | antibiotic | 10 cc |
| (7) | antifungal* | |
| (8) | water wetting agent* | |

*If using a commercially available antifungal or water wetting agent, one should select the amount, in proportion to the other components, recommended by the manufacturer.

according to the present invention that may be applied to the surface of the trees or other plants and shrubs.

(1a) For trees the antibiotic must be injected. Also for trees or lumber the amounts and ingredients may vary according to the target insect. An example would be termites in a house will not be feeding on living wood so no antihistamine will be required.

(1b) For insects attacking the foliage, such as leaf miners or elm beetles ingredients 1, 2, 3 and 4 may be found to do the job. In the case of the elm beetle the same mixture should be effective in flushing them from there winter hiding spots.

(1c) For a fungal or bacterial attack on plants such as roses or gardenias a mixture consisting of 2, 6 and 7 is useful however a second spraying may be required and in an extreme case even a third spraying may be needed. Use of the dry fungicide as well as the ground is one of the sources of reinfection. In plants or shrubs that have been hollowed out by infection, the addition of ingredient 5 is recommended. This treatment should be renewed yearly.

(1d) To discourage an insect infestation of a tree or shrub or area a mixture of 1, 3, 4 and 8 may be used in a reduced strength as the purpose is to keep them away not to flush them out.

In every case the tree or other plant must be built up. This can be done by fertilizing the plant with a long term fertilizer best suited to that plant type. Where applicable water may needed to be applied for an extended period. This may not be practical in the case of a forest. As much of the building up process as possible should be done before treatment. This would apply in the case of a suspected direction for a future infestation or infection. For an existing infestation or infection speed is the key.

Among the insects which the inventor believes may be controlled through the present invention are the Western Pine Beetle, Spruce Beetle, Southern Pine Beetle, Jeffrey Pine Beetle, Mountain Pine Beetle, Douglas-Fir Beetle, Spruce Beetle, Black Turpentine Beetle, Red Turpentine Beetle, Small Southern Pine Engraver, Sixspined Ips, Eastern Fivespined Ips, Northern Spruce Engraver Beetle, Pine Engraver, Western Balsam Bark Beetle, Fir Engraver, Clerid Beetle, Eastern Ash Bark Beetle, Native Elm Bark Beetle, Smaller European Elm Bark Beetle, Hickory Bark Beetle, Red-haired Pine Bark Beetle, Hylurgops palliatus (Gyllenhal), Six-toothed Bark Beetle, Spruce Engraver Beetle, Mediterranean Pine Engraver Beetle, Spruce Wood Engraver, and Common Pine Shoot Beetle. The WebPage "www.foestryimages.org" discloses a good deal of valuable information regarding particular insects and is incorporated herein by reference.

What is claimed is:

1. A method for protecting a tree from insects comprising the steps of injecting the tree with a fungicide and/or an antibiotic, and
applying a composition to the surface of the tree, said composition comprising water, an insect repellent, an antihistamine, and an insect poison.

2. The method according to claim 1, wherein the tree is a pine.

3. The method according to claim 1 or 2, wherein the insect is the Pine Bark Beetle.

4. The method according to claim 1, wherein the insect repellent is Wintergreen.

5. The method according to claim 1, wherein the insect repellent is Oil of Mint.

6. The method according to claim 1, wherein the antihistamine is diphenhydramine hydrochloride.

7. The method according to claim 3, wherein the poison is malathion.

8. The method according to claim 1, wherein the poison is diazinon.

9. The method according to claim 1, wherein the poison is dursban.

10. The method according to claim 1, wherein the poison is sevin.

11. The method according to claim 1, wherein the antibiotic is a cephalosporin.

12. The method according to claim 1, wherein the antibiotic is cephalexin.

13. The method according to claim 1, wherein the antibiotic is penicillin.

14. The method according to claim 1, wherein the antibiotic is tetracycline.

15. A method for protecting a tree from insects comprising the steps of injecting the tree with penicillin, and
applying a composition to the surface of the tree, said composition comprising water, Wintergreen, diphenhydramine hydrochloride, and malathion.

16. The method according to claim 1, wherein the antibiotic is a sulfa drug.

* * * * *